United States Patent [19]

Nishihira et al.

[11] Patent Number: 5,916,921

[45] Date of Patent: *Jun. 29, 1999

[54] THERAPEUTIC AGENTS FOR LIVER REGENERATION

[75] Inventors: Tetsuro Nishihira; Hideyuki Doi, both of Miyagi-ken; Hiromichi Komatsu, Nagano-ken, all of Japan

[73] Assignee: Chugai Seiyaku Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,814

[22] PCT Filed: Jun. 7, 1995

[86] PCT No.: PCT/JP95/01136

§ 371 Date: Dec. 18, 1996

§ 102(e) Date: Dec. 18, 1996

[87] PCT Pub. No.: WO96/00059

PCT Pub. Date: Jan. 4, 1996

[30] Foreign Application Priority Data

Jun. 23, 1994 [JP] Japan .................... 6-141998

[51] Int. Cl.$^6$ .................................................. A61K 31/195
[52] U.S. Cl. ............................................................. 514/561
[58] Field of Search ............................................... 514/561

[56] References Cited

U.S. PATENT DOCUMENTS 4,259,353  3/1981  Kleinberger ............................ 424/319
4,499,076  2/1985  Ohashi et al. ........................... 424/143

FOREIGN PATENT DOCUMENTS 54-89014  7/1979  Japan .

OTHER PUBLICATIONS

Fujiwara et al, "Evaluation of Administration Ratio of BCAA Enriched Solution in Partially Hepatectomized Rats", *Journal of Japan Vein–Enteral Nutrition Research Society*, No. 4:104–107 (Feb. 1989).

*Primary Examiner*—Phyllis G. Spivack
*Attorney, Agent, or Firm*—Browdy and Neimark

[57] ABSTRACT

A therapeutic agent for liver regeneration which contains valine as an active ingredient is disclosed that is effective against hepatopathy in hepatitis, fatty liver and drug-induced liver disorders. The agent promotes liver regeneration and recovery to normal liver function. It is also capable of inducing rapid-operative recovery of patients who were hepatectomized due to gallbladder cancer, liver cancer and metastatic liver cancer.

7 Claims, No Drawings

THERAPEUTIC AGENTS FOR LIVER REGENERATION

This case is a 371 of PCT/JP95/01136 filed Jun. 7, 1995.

TECHNICAL FIELD

This invention relates to therapeutic agents for liver regeneration containing valine, which is a branched-chain amino acid, as an active ingredient. To be more precise, the invention relates to valine-containing preparations that are capable of regenerating hepatocytes in cases such as after the removal of the liver due, for example, to hepatopathy, hepatitis and cirrhosis.

BACKGROUND ART

Some factors and drugs are known to have a hepatocyte regenerating action. For example, Archive of Pathology, 16, 226–231 (1993) teaches that when a diet containing 1 wt % of a dried thyroid gland powder was continuously fed after partial hepatectomy, the liver weight increased significantly over the control from the seventh day of the partial hepatectomy.

Journal of Biological Chemistry, 247, 1757–1766 (1972) reports that a liquid mixture of triiodothyronine (T3), mixed amino acids in solution, glucagon and heparin caused DNA synthesis in the liver.

In addition, a growth factor for the primary culture of hepatocytes in mature rats was purified from rat sera 24 hours after 70% partial hepatectomy and designated HGF (hepatocyte growth factor) or hepatotropin, as described in Biochemical and Biophysical Research Communications, 122, 1450–1459 (1984).

Insulin and glucagon are also important factors to liver regeneration, as described in Advances in Enzyme Regulation, 13, 281–293 (1975), and in Japan, ever since Okita et al. reported the application of an insulin-glucagon therapy to fulminating hepatitis in Gastroenterologia Japan., 14, 453 (1979), they have been commonly used in clinical cases.

Valine, isoleucine and leucine, which are branched-chain amino acids, have been reported to be capable of ameliorating hepatic encephalopathy and septic encephalopathy or saving proteins during invasion, and Hepatoamine (registered trademark), Hepan (registered trademark), Aminoleban (registered trademark), Amiparen (registered trademark), Amizet (registered trademark) and Aminic (registered trademark) are commercially available as amino acids in solution. However, it is entirely unknown that valine has a hepatocyte regenerating action.

In recent years, hepatocyte growth factor (HGF) was purified from rats and humans, followed by successful cloning of cDNA, and in view of its capability for proliferating primary cultured hepatocytes, as well as the results of increased blood HGF activity in hepatopathy and induced expression of HGF mRNA, clinical application of the HGF is expected to materialize in the future but, as of today, this has not been commercialized.

The only treatment that is presently held in Japan to have a liver regenerating effect is glucagon-insulin therapy (GI therapy). However, the effectiveness of this GI therapy has not yet been recognized in Europe and the United States of America.

DISCLOSURE OF INVENTION

The object of the present invention is to provide a drug that is safe and which exhibits a potent liver regenerating effect on diseases of the liver that involves various degrees of hepatopathy.

In order to attain this object, various concentrations of valine were given to rats. The effects of valine on the weights of the livers and the histopathological findings were analyzed. As a result, the present inventors found that valine caused marked liver regeneration, which led to the accomplishment of the present invention.

The valine to be used in the invention may be commercially available or synthesized products and any types of valine can be employed irrespective of the method of their preparation. In addition, either of D-, L- and DL-forms of valine is usable.

BEST MODE FOR CARRYING OUT THE INVENTION

When the valine is used as a therapeutic agent for liver regeneration, it is generally preferred to perform intravenous administration, but other routes of administration such as peroral and parenteral are also possible. Valine may be used singly as a preparation in which it is the sole ingredient, but preferably it is used either in combination with a preparation for infusion such as a high-calorie drug for infusion or as an addition to an infusion preparation.

Possible dosage forms for administration include liquids, suspensions, emulsions, tablets, capsules, granules, subtilized granules, particulate matter, powders and suppositories. In order to prepare these dosage forms, pharmaceutically acceptable, liquid or solid, suitable auxiliary agents are preferably added, as exemplified by excipients, fillers, extenders, solvents, emulsifiers, lubricants, flavor correctives, flavoring agents, dyes and buffering substances.

The therapeutic agent for liver regeneration of the invention is applicable to patients who had livers tissue removed due, for example, to hepatitis, cirrhosis and liver cancer, and the dose of its administration varies with the sex, physique, constitution, age and symptom of the patient, as well as the dosage form to be used; the valine concentration is suitably selected from the range of 0.5–5.0% if the therapeutic agent is to be administered as a preparation for amino acid infusion through peripheral or central veins, from the range of 1.0–10.0% in the case of an ampule to be added to a preparation for infusion, and from the range of 5.0–100% in the case of suspensions, emulsions, tablets, capsules, granules, subtilized granules, particulate matter, powders, suppositories and other dosage forms for administration perorally or through the intestines.

It should be noted that the percentage of valine concentration in the invention means "w/v %" if the valine is in a liquid form and "w/w %" if it is in a solid form.

EXAMPLES

The following examples are provided for further illustrating the present invention.

Example 1

Effect of Increased Valine on the Liver Regeneration in 70% Hepatectomized Rats

Eight- to nine-week old Donryu male rats weighing about 250 g (5–7 animals per group), which were anesthetized with ether while a catheter was inserted and retained in a central vein, got laparotomy and had about 70% of the liver removed to prepare 70% hepatectomized model rats. The catheter was passed through a subcutaneous tunnel to span both blade bones, equipped with a harness and connected to a swivel via a protective coil. The rats were transferred into a metabolic cage, acclimated for infusion by treatment with a lactated Ringer's injection (LACTEC, registered trademark of Otsuka Pharmaceutical Co., Ltd.) and continuously administered for 3 or 5 days with a high-calorie fluid for infusion (see below) in an amount of 220 kcal/kg/day as calculated for non-protein colonies and with the pumpforced administration rate being set at 250 ml/kg/day: a 100% group (control group) was administered a high-calorie fluid for infusion consisting of a 10% amino acid complex preparation (MORIPRON, registered trademark of Morishita Roussel Co., Ltd.) supplemented with glucose, electrolytes, trace metals and vitamins (valine concentration=2.25 g/L); a 0% group was administered the same fluid as for the control, except that it was free of valine (valine concentration=0 g/L); a 200% group was administered the same fluid as for the control, except that it contained an additional amount of L-valine (Japanese Pharmacopeia) (valine concentration=4.50 g/L); and a 400% group was administered the same fluid as for the control, except that it also contained an additional amount of L-valine (Japanese Pharmacopeia) (valine concentration= 9.00 g/L).

At the end of each infusion, the body weight of each animal was measured. After exsanguinating from the abdominal aorta under anesthetization with ether, the liver was removed and weighted. And then, specimen of the liver was taken for histopathological examination. The liver to body weight ratio was determined based on the results of measurement of the liver and body weights. In addition, the liver was fixed with formalin and subjected to hematoxylin-eosin double stain to prepare specimens for histopathological testing. The results of measurements were represented by mean±standard deviation (SD) and processed statistically by a Student's T test, in which the result was held to be "significantly different" at $p<0.05$. The data on the liver weight and the liver to body weight ratio are set forth in Table 1.

In the histopathological testing of the liver, the expansion of the glycogen field and the formation of vacuoles in hepatocytes were significant in the 0% group; however, none of the cases in the other groups had any recognizable abnormality and all of them gave the normal morphological image.

Example 2

Effect of Valine on the Growth of Pro-Fat Cells

Pro-fat cells derived from the skin of C3H female mice were used to investigate the effect of valine on cell growth. The pro-fat cells were cultured on 96-well flat bottom plates at a concentration of $1 \times 10^4$ cells/well or $2.5 \times 10^4$ cells/well, with the valine concentration being varied at 80 mg/L, 160 mg/L or 320 mg/L. After impulsing of $^3$H-thymidine, the thymidine uptake was measured with a scintillation counter. The culture medium was RPMI 1640. The results are shown in Table 2.

TABLE 2

| | [$^3$H] thymidine uptake (cpm) | |
|---|---|---|
| Group | cell count: $1 \times 10^4$ cells | cell count: $2.5 \times 10^4$ cells |
| 100% (80 mg/L)* | 1203.3 | 2771.1 |
| 200% (160 mg/L)* | 1314.4 | 3441.1 |
| 400% (320 mg/L)* | 3180.0 | 4678.9 |

*: Valine concentration in liquid culture.

TABLE 1

| | Continuously Administered for 3 days | | | Continuously Administered for 5 days | | |
|---|---|---|---|---|---|---|
| Group | Number of cases | Liver weight (g) | Liver to body weight ratio (%) | Number of cases | Liver weight (g) | Liver to body weight ratio (%) |
| 0% (0 g/L)# | 5 | 5.6 ± 0.5 [1.00] | 2.2 ± 0.1 [0.96] | 7 | 6.3 ± 2 [1.03] | 2.4 ± 0.1 [1.04] |
| 100% (control group) (2.25 g/L) | 5 | 5.6 ± 0.3 [1.00] | 2.3 ± 0.2 [1.00] | 6 | 6.1 ± 0.3 [1.00] | 2.3 ± 0.1 [1.00] |
| 200% (4.50 g/L) | 5 | 6.8 ± 0.3** [1.21] | 2.6 ± 0.2* [1.13] | 6 | 7.6 ± 0.3** [1.25] | 2.9 ± 0.02** [1.26] |
| 400% (9.00 g/L) | 5 | 7.5 ± 0.3** [1.34] | 2.9 ± 0.1 [1.26] | 7 | 8.6 ± 0.3** [1.41] | 3.1 ± 0.1** [1.35] |

: Valine concentration in high-calorie fluid for infusion.
Statistically analyzed by a Student's T test mens ± S.D. *:$p < 0.05$ **:$p < 0.01$ (vs control group)
Figures in brackets are relative values with the control group taken as unity.

After the 3-day administration, the liver weight was 5.6±0.3 g in the control group, whereas the 200% group gave a value of 6.8±0.3 g and the 400% group a value of 7.5±0.3 g, both of which were significantly ($p<0.01$) higher; after the 5-day administration, the control group showed a value of 6.1±0.3 g whereas the 200% group gave a value of 7.6±0.3 g and the 400% group a value of 8.6±0.3 g, both of which were significantly ($p<0.01$) higher.

After the 3-day administration, the liver to body weight ratio was 2.3±0.2% in the control group, whereas the 200% group gave a value of 2.6±0.2% which was significantly ($p<0.05$) higher and the 400% group a value of 2.9±0.1% which was also significantly ($p<0.01$) higher; after the 5-day administration, the control group showed a value of 2.3±0.1% whereas the 200% group gave a value of 2.9±0.2% and the 400% group a value of 3.1±0.1%, both of which were significantly ($p<0.01$) higher.

As is obvious from Table 2, the thymidine uptake increased with the increasing valine concentration.

Example 3

Effect of Valine on the Growth of Primary Cultured Hepatocytes

Eight- to nine-week old Donryu male rats weighing about 250 g were incised through the abdominal wall under anesthetization with ether to have 70% of the liver removed. Three days later, the liver of the anesthetized rats was perfused with collagen and the freed hepatocytes were collected. The hepatocytes were inoculated on collagen-coated 92-well flat bottom plates at a concentration of $2 \times 10^4$ cells/well. The valine concentration was set at 50 mg/L, 100 mg/L or 200 mg/L, and after 36-h cultivation, $^3$H-thymidine was impulsed and the thymidine uptake was measured with a scintillation counter. The culture medium was Williams Media E, which was supplemented with 10% FCS, $10^{-6}$M dexamethazone and $10^{-7}$M insulin. The data on thymidine uptake are shown in Table 3.

TABLE 3

| Group | [$^3$H] thymidine uptake (cpm) cell count: 2 × 10$^4$ cells |
|---|---|
| 100% (50 mg/L)* | 1276.2 |
| 200% (100 mg/L)* | 1339.2 |
| 400% (200 mg/L)* | 1991.5 |

*: Valine concentration in liquid culture.

As is obvious from Table 3, the thymidine uptake of the primary cultured hepatocytes increased with the increasing valine concentration, showing the effectiveness of valine in the growth of cultured hepatocytes.

INDUSTRIAL APPLICABILITY

The therapeutic agent for liver regeneration of the invention is effective against hepatopathy in hepatitis, fatty liver and drug-induced liver disorders by promoting liver regeneration and recovering the normal liver functions. It is also capable of inducing early liver regeneration to thereby achieve rapid post-operative recovery of patients who were hepatectomized due, for example, to gallbladder cancer, liver cancer and metastatic liver cancer. These actions of the therapeutic agent are further enhanced if it is used in combination with high-calorie fluids for infusion and even in hepatectomized patients suffering from chronic hepatitis or cirrhosis, the agent achieves rapid liver regeneration to thereby enable safe operations and rapid post-operative recovery.

We claim:

1. A method of inducing liver regeneration comprising administering to a patient in need of said therapy an amount sufficient for said therapy of a composition containing valine as an active ingredient and which contains substantially no other amino acid.

2. A method of inducing liver regeneration according to claim 1 by venous infusion to said patient, said composition consisting essentially of valine in a concentration of 0.5 to 5.0% in a pharmaceutical excipient in liquid form suitable for infusion through peripheral or central veins.

3. A method according to claim 1 wherein said administration is by the oral route, and wherein said composition consists essentially of valine in an amount of at least 5% by weight in an orally acceptable pharmaceutical carrier.

4. A method according to claim 1 wherein said valine is L-valine.

5. A method according to claim 1 wherein said composition consists essentially of said valine and at least one of a pharmaceutically acceptable excipient, filler, extender, solvent, emulsifier, lubricant, flavor corrective, flavoring agent, dye or buffering substance.

6. A method according to claim 1 wherein said patient is a person who has had his or her liver removed.

7. A method according to claim 1 wherein said patient is a person who has been hepatectomized due to gallbladder cancer, chronic hepatitis, cirrhosis, liver cancer or metastatic liver cancer.

* * * * *

UNITED STATES PATENT AND TRADEMARK OFFICE
CERTIFICATE OF CORRECTION

PATENT NO. : 5,916,921
DATED : Jun. 29, 1999
INVENTOR(S) : Nishihira et al.

It is certified that error appears in the above-identified patent and that said Letters Patent is hereby corrected as shown below:

Col. 6, line 27 (Claim 6), delete "had his or her liver removed" and insert therefor --been hepatectomized--.

Signed and Sealed this

Twenty-eighth Day of December, 1999

Q. TODD DICKINSON

*Attest:*

*Attesting Officer*  *Acting Commissioner of Patents and Trademarks*